(12) United States Patent
Fuchs et al.

(10) Patent No.: US 9,470,986 B2
(45) Date of Patent: Oct. 18, 2016

(54) INSPECTION METHODS, INSPECTION APPARATUSES, AND LITHOGRAPHIC APPARATUSES

(71) Applicant: ASML Netherlands B.V., Veldhoven (NL)

(72) Inventors: Andreas Fuchs, Meerbusch (DE); Maurits Van Der Schaar, Eindhoven (NL); Scott Anderson Middlebrooks, Duizel (NL); Panagiotis Pieter Bintevinos, Best (NL)

(73) Assignee: ASML Netherlands B.V., Veldhoven (NL)

( * ) Notice: Subject to any disclaimer, the term of this patent is extended or adjusted under 35 U.S.C. 154(b) by 2 days.

(21) Appl. No.: 14/190,036

(22) Filed: Feb. 25, 2014

(65) Prior Publication Data
US 2014/0176955 A1 Jun. 26, 2014

Related U.S. Application Data

(63) Continuation of application No. 12/902,341, filed on Oct. 12, 2010, now Pat. No. 8,749,786.

(60) Provisional application No. 61/267,633, filed on Dec. 8, 2009.

(51) Int. Cl.
G03F 7/20 (2006.01)
G01N 21/956 (2006.01)

(52) U.S. Cl.
CPC ......... *G03F 7/70633* (2013.01); *G01N 21/956* (2013.01)

(58) Field of Classification Search
CPC .................................................. G03F 7/70633
See application file for complete search history.

(56) References Cited

U.S. PATENT DOCUMENTS

| 4,780,617 A | 10/1988 | Umatate et al. |
| 5,745,242 A | 4/1998 | Hata |

(Continued)

FOREIGN PATENT DOCUMENTS

| EP | 1 628 164 A2 | 2/2006 |
| WO | WO 2009/078708 A1 | 6/2009 |

OTHER PUBLICATIONS

Weisstein, Eric W. "Polynomial." From MathWorld—A wolfram Web Resource. http://mathworld.wolfram.com/Polynomial.html (printed Apr. 5, 2016).*

(Continued)

*Primary Examiner* — Kara E Geisel
*Assistant Examiner* — Shawn Decenzo
(74) *Attorney, Agent, or Firm* — Sterne, Kessler, Goldstein & Fox P.L.L.C.

(57) ABSTRACT

A method for determining overlay error includes measuring asymmetry of radiation reflected from each of a plurality of targets on a substrate. The plurality of targets include a predetermined overlay offset. The method also includes comparing the measured asymmetry of the radiation reflected from each of the plurality of targets to the corresponding predetermined overlay offset of the respective target. Additionally, the method includes determining the overlay error of a point on the substrate as a function of measured asymmetry reflected from the point. The function is determined by fitting a polynomial or a Fourier series to a comparison of the measured asymmetry of the radiation reflected from each of the plurality of targets to the corresponding predetermined overlay offset of the respective target. The function limits an effect of linearity error.

16 Claims, 6 Drawing Sheets

(56) References Cited

U.S. PATENT DOCUMENTS

| | | |
|---|---|---|
| 6,269,322 B1 | 7/2001 | Templeton et al. |
| 6,297,876 B1 | 10/2001 | Bornebroek |
| 6,436,595 B1 | 8/2002 | Credendino et al. |
| 6,768,539 B2 | 7/2004 | Gui et al. |
| 6,949,462 B1 | 9/2005 | Yang et al. |
| 6,961,116 B2 | 11/2005 | Den Boef et al. |
| 6,982,793 B1 | 1/2006 | Yang et al. |
| 6,985,229 B2 | 1/2006 | Lee et al. |
| 7,046,361 B1 | 5/2006 | Yang et al. |
| 7,193,715 B2 | 3/2007 | Smedt et al. |
| 7,230,704 B2 | 6/2007 | Sezginer et al. |
| 7,230,705 B1 | 6/2007 | Yang et al. |
| 7,333,200 B2 | 2/2008 | Sezginer et al. |
| 7,379,184 B2 | 5/2008 | Smith et al. |
| 7,385,699 B2 | 6/2008 | Mieher et al. |
| 7,391,513 B2 | 6/2008 | Van Der Schaar et al. |
| 7,433,040 B2 | 10/2008 | Mieher et al. |
| 7,561,282 B1 | 7/2009 | Widmann |
| 7,564,557 B2 | 7/2009 | Mieher et al. |
| 7,573,584 B2 | 8/2009 | Den Boef et al. |
| 7,715,007 B2 | 5/2010 | Brill et al. |
| 7,746,446 B2 | 6/2010 | Okita |
| 8,149,387 B2 | 4/2012 | Alberti et al. |
| 8,243,273 B2 | 8/2012 | Levinski et al. |
| 8,749,786 B2 | 6/2014 | Fuchs et al. |
| 2007/0035712 A1* | 2/2007 | Gassner ............... G03F 7/70666 355/55 |
| 2007/0291269 A1 | 12/2007 | Van Der Schaar et al. |
| 2008/0144036 A1 | 6/2008 | Schaar et al. |
| 2008/0227228 A1* | 9/2008 | Huang ............... H01L 22/12 438/16 |
| 2009/0063378 A1* | 3/2009 | Izikson ............... G05B 13/027 706/21 |
| 2009/0073448 A1 | 3/2009 | Tenner et al. |
| 2009/0087756 A1 | 4/2009 | Schulz |
| 2009/0180095 A1 | 7/2009 | Alberti et al. |
| 2011/0134419 A1 | 6/2011 | Fuchs et al. |
| 2011/0196646 A1 | 8/2011 | Mos et al. |
| 2011/0255066 A1 | 10/2011 | Fuchs et al. |

OTHER PUBLICATIONS

"Diffractive overlay measurement method for scatterometer, involves fitting straight line to data approximate to real overlay versus asymmetry curve for small overlay values by utilizing known overlay difference," Research Disclosure RD 533012 A, last accessed on Dec. 11, 2013; 1 page.

Non-Final Rejection mailed Jan. 16, 2013 for U.S. Appl. No. 12/902,341, filed Oct. 12, 2010; 19 pages.

Final Rejection mailed Jun. 14, 2013 for U.S. Appl. No. 12/902,341, filed Oct. 12, 2010; 23 pages.

Notice of Allowance mailed Nov. 8, 2013 for U.S. Appl. No. 12/902,341, filed Oct. 12, 2010; 12 pages.

Corrected Notice of Allowability mailed Nov. 29, 2013 for U.S. Appl. No. 12/902,341, filed Oct. 12, 2010; 6 pages.

Notice of Allowance mailed Feb. 7, 2014 for U.S. Appl. No. 12/902,341, filed Oct. 12, 2010; 8 pages.

\* cited by examiner

INSPECTION METHODS, INSPECTION APPARATUSES, AND LITHOGRAPHIC APPARATUSES

This application incorporates by reference in their entireties U.S. patent application Ser. No. 12/902,341, filed Oct. 12, 2010, and U.S. Provisional Patent Application No. 61/267,633, filed Dec. 8, 2009.

BACKGROUND

1. Field of the Invention

The present invention relates to methods of inspection usable, for example, in the manufacture of devices by lithographic techniques

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, it is necessary to measure parameters of the patterned substrate, for example the overlay error between successive layers formed in or on it. There are various techniques for making measurements of the microscopic structures formed in lithographic processes, including the use of scanning electron microscopes and various specialized tools. One form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Devices are built up layer by layer and overlay is a measure of a lithographic apparatus' ability to print these layers accurately on top of each other. Successive layers or multiple processes on the same layer must be accurately aligned to the previous layer, otherwise electrical contact between structures will be poor and the resulting devices will not perform to specification. Overlay is a measure of the accuracy of this alignment. Good overlay improves device yield and enables smaller product patterns to be printed. The overlay error between successive layers formed in or on the patterned substrate is controlled by various parts of the exposure apparatus (of the lithographic apparatus). It is mostly the alignment system of the lithographic apparatus that is responsible for the alignment of the radiation onto the correct portions of the substrate.

Overlay may be measured using an "image-based" (box-in-box) technique or Diffraction-Based Overlay (DBO) metrology. DBO is an emerging metrology technique used because of its superb TMU (Total Measurement Uncertainty) compared to "image-based" techniques. In the "image-based" case, overlay may be derived from a measurement of the position of a resist marker pattern relative to a marker pattern in an earlier formed product layer. In the DBO case, overlay is indirectly measured, for example by detecting variations in diffracted intensities of two overlapping periodic structures such as a top resist grating stacked over a product layer grating.

Diffraction based overlay (DBO) usually measures differences in intensity between positive and negative diffraction orders (asymmetry) obtained from a radiation source beamed upon a grating or similar structure. The grating is made up of at least two overlaid layers, and the resulting diffraction orders should be symmetrical if there is no overlay offset between the two layers. Where there is asymmetry, the coherence between these asymmetries and overlay numbers is typically a recurrent function with unknown shape depending on stack and the illumination conditions. For small overlay values, this shape can be approximated by approximately linear region of a first order sine curve. Consequently, for such small overlay values, the asymmetry can be assumed to be proportional to the overlay: $A = K \times OV$. However, for overlay errors greater than 15 nm this fit is not valid anymore and leads to significant measurement errors

SUMMARY

It is desirable to provide a system to address the above problem.

According to an aspect of the present invention, there is provided a method to determine an overlay error on a substrate comprising: projecting a beam of radiation onto three or more targets, each comprising first and second overlapping patterns with predetermined overlay offsets, on the substrate, measuring the asymmetry of the radiation reflected from each target on the substrate, and determining the overlay error not resultant from the predetermined overlay offsets, determining a function to enable calculation of overlay from asymmetry for other points on the wafer, where the determining the function includes limiting the effect of linearity error when determining the overlay error from the function.

According to a second aspect of the present invention, there is provided inspection apparatus for measuring an overlay error on a substrate comprising three or more targets, each target comprising first and second overlapping patterns with predetermined overlay offsets, the inspection apparatus comprising: a projection system configured to project a radiation beam onto each of the targets, a detector configured to detect second radiation having interacted with the targets, and a processor configured to determine the lateral overlay using the detected second radiation thereby determining the overlay error not resultant from the predetermined overlay offsets, and to determine a function to enable calculation of overlay from asymmetry for other points on the wafer while limiting the effect of linearity error when determining the overlay error from the function.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

Figure 1:
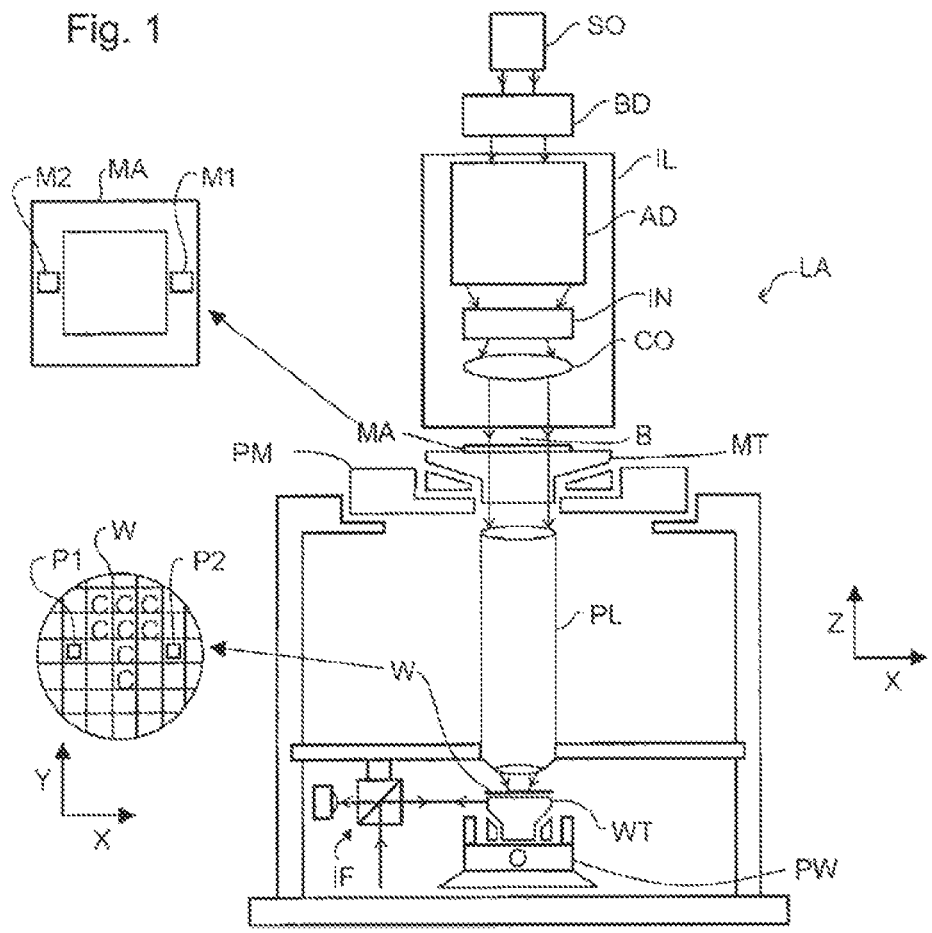
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist-coated wafer) W and connected to a second positioner PW configured to accurately position the substrate in accordance with certain parameters; and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
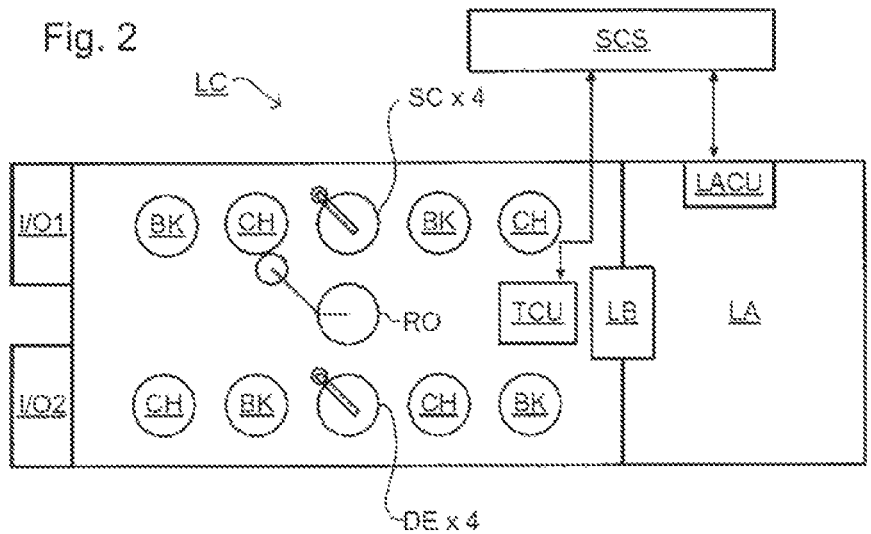
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
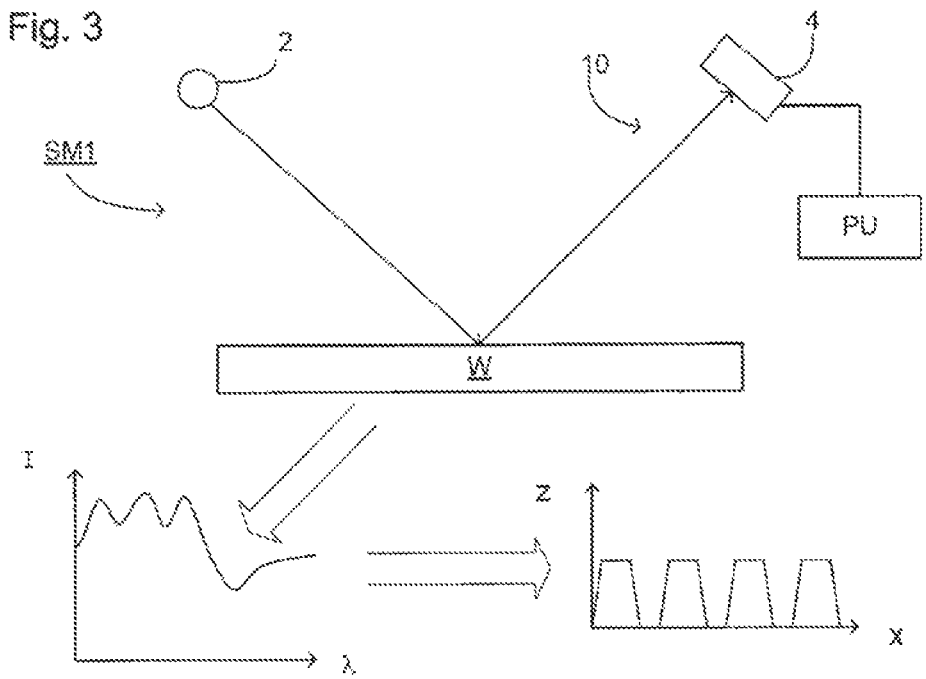
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
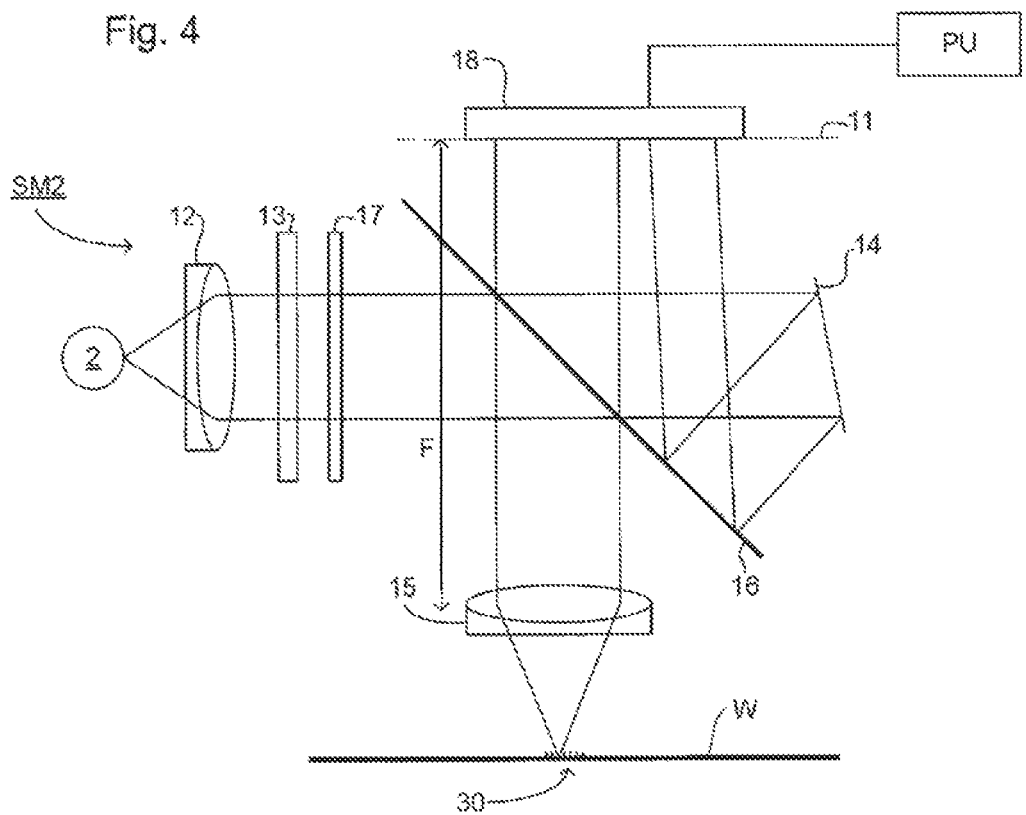
FIG. 4 depicts a second scatterometer.

Another scatterometer that may be used with the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflective surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18.

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least $2\Delta\lambda$ (i.e., twice the bandwidth).

Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be (a) a resist layer grating, which is printed such that after development, the bars are formed of solid resist lines, or (b) a product layer grating, or (c) a composite grating stack in an overlay target structure comprising a resist grating overlaid or interleaved on a product layer grating. The bars may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the grating, such as line widths and shapes, may be input to the reconstruction process, performed by processing unit PU, from knowledge of the printing step and/or other scatterometry processes.

Figure 5:
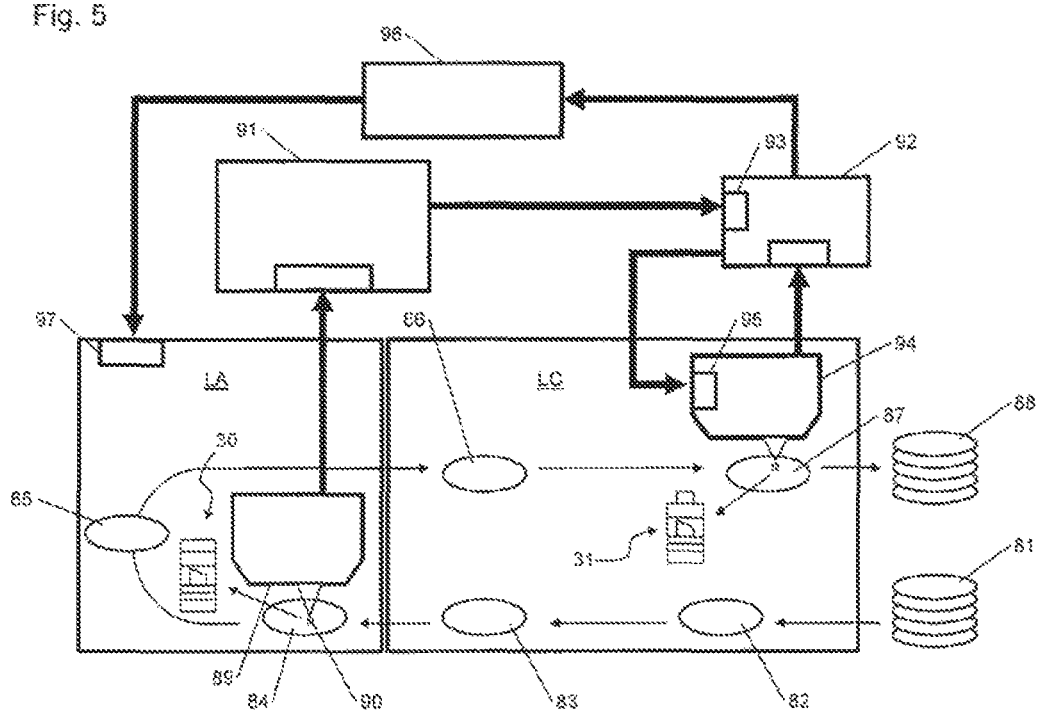
FIG. 5 depicts a lithographic cell.

With reference to FIG. 5, the exposure or lithographic apparatus LA and lithographic cell LC process a batch of input wafers 81 through various steps 82 to 87 to a set of output wafers 88. A wafer introduced into the track 82 is processed through spin coating step 83 before passing into the exposure apparatus LA. In the alignment step 84, the phase grating alignment sensor 89 projects a beam of light onto the product layer grating 90 on the wafer and detects the light scattered by the grating. The phase grating alignment sensor is a special kind of scatterometer in that it derives position information by measuring the phase difference between diffraction orders that are diffracted by the pattern on the substrate. This is what distinguishes an alignment sensor from a typical scatterometer since a typical scatterometer normally measures only intensity or polarization state of diffracted orders without considering the phase difference between different diffraction orders.

The asymmetry processor 91 determines the asymmetry of the product grating from the properties of the scattered light and feeds information about the product grating asymmetry forward to the subsequent overlay measurement. The wafer 85 is exposed with an overlay marker along with a product pattern and the resist is developed 86 to print the overlay marker on the wafer stacked on top of the product grating.

The asymmetry information is fed forward to the overlay calculation processor 92. The overlay calculation processor 92 has a receiving module 93 that receives the information about the product grating asymmetry. The information may comprise a model of the product grating profile constructed by the asymmetry processor 91. Alternatively, the overlay calculation processor 92 itself may construct a model of the product grating profile using the received information about the product grating asymmetry. In either case, the overlay calculation processor 92 constructs a model of the stacked product and overlay grating profile using or incorporating a model of the product grating profile. The stack model is then used to determine the overlay offset and use of the asymmetry information minimizes the effect of the asymmetry on the overlay offset measurement.

The metrology tool or inspection apparatus comprises scatterometer opto-mechanical sensor hardware 94 that projects a beam of light onto the stacked product and resist grating on the wafer. It detects the light that has interacted with the product and overlay gratings by scattering.

The scatterometer sensor hardware 94 may have an interface 95 that receives control signals from the overlay calculation processor 92. The instructions cause the scatterometer sensor 94 to adjust its measurement settings. The asymmetry information is thus used by the calculation processor to configure the wavelength and/or polarization of the beam of light so as to minimize the effect of the asymmetry on the overlay measurement. In addition, or alternatively, the information may be used to configure the detector in the scatterometer for the same purpose.

The overlay calculation processor 92 determines the overlay from the properties of the scattered light detected in the scatterometer sensor hardware 92. The overlay offset data is fed to a controller 96 that feeds corrections back to the feedback receiving module 97 of the exposure apparatus LA for correction of errors in the overlay, for example by feeding corrections into the alignment system.

Thus the product layer gratings 90 on the wafer are measured with the alignment sensor 89 before the resist is exposed at step 85. These product layer gratings 90 may also be used for wafer alignment.

The measurement by the alignment sensor 89 at step 84 may include one or more of the following measurements that are indicative of the presence of grating asymmetry:

1. measuring position variations for various wavelengths (position shift between colors);
2. measuring position variations for various orders (position shift between diffraction orders); and
3. measuring position variations for various polarizations (position shift between polarizations).

This data can for example be obtained with any type of alignment sensor, for example a SMASH (SMart Alignment Sensor Hybrid) sensor, as described in U.S. Pat. No. 6,961,116 that employs a self-referencing interferometer with a single detector and four different wavelengths, and extracts the alignment signal in software, or Athena (Advanced Technology using High order ENhancement of Alignment), as described in U.S. Pat. No. 6,297,876, which directs each of seven diffraction orders to a dedicated detector, which are both incorporated by reference herein in their entireties.

There is a strong demand especially for applications to control litho scanner performance when using diffraction based overlay (DBO) techniques to measure overlay up to 100 nm with an accuracy of 1 nm. Knowing the linearity error is very important for DBO when overlay is 15 nm or greater, as this is significantly off the linear approximation of the calibration curve. Knowing the linearity error allows proper selection of illumination settings where this error is minor and/or to enable correction algorithms. Illumination settings may include illumination wavelengths and polarization, aperture settings etc.

Currently linearity errors can only be identified by comparing the diffraction based overlay numbers with either numbers from an image based overlay tool or by exposing wafers with well defined overlay numbers. Both methods are typically not acceptable, as they either require an extra metrology tool for reference, or extra calibration wafers that need to be generated for each stack/process/variation (which leads to a huge overhead). Furthermore, both these methods are affected by noise/measurement uncertainties ruining the accuracy of the DBO tool.

Instead, it is proposed to calibrate for the non-linearity over the calibration by using targets with part structures on the reticle having intentionally introduced or "programmed" overlay. Programming a bias or overlay allows determination of the curve of asymmetry (what is measured) against the unknown overlay error. The more of these programmed offset points, the better the determination These targets need to be adjacent to each other (to fulfill the assumption that they are all affected by the same scanner overlay error) and need to represent the full overlay range that is demanded. Therefore each target may have a different overlay programmed, such that the programmed overlays comprise an arithmetic series, having for example, a difference of 20 nm between the programmed overlay of each target.

Figure 6:
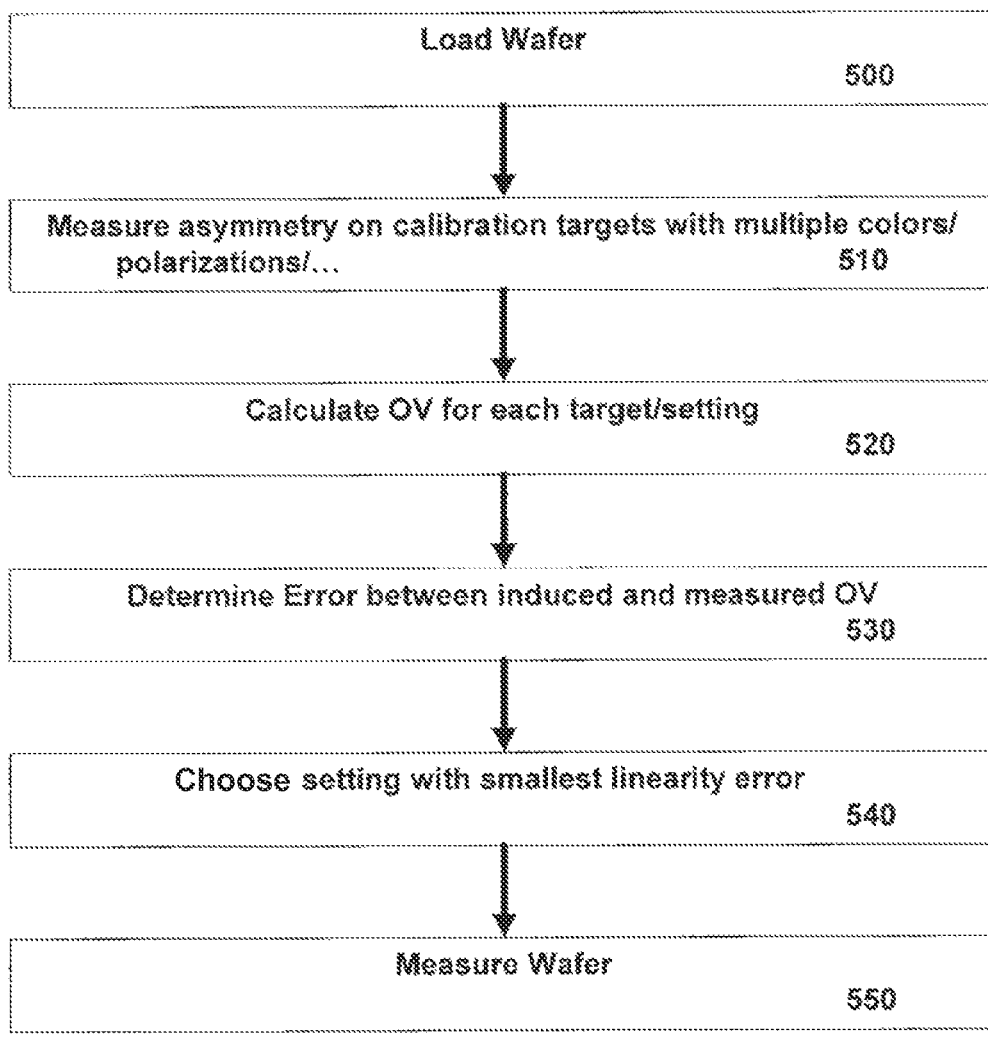
FIG. 6 is a flowchart illustrating a method according to a first embodiment of the invention.

FIG. 6 is a flowchart illustrating a first method according to an embodiment of the invention. Table 1 shows example values at certain stages of the method. Firstly a wafer is loaded 500 and then, in a calibration routine (e.g., lot overhead), the asymmetry of these targets is measured 510 and the overlay is calculated 520 for a number of different illumination settings. For this case overlay targets are used, having a positive and a negative bias around a programmed overlay offset. The target which measures the smallest overlay is taken as reference (as it is measured with the best accuracy). From this measured small overlay, and the known programmed overlay of its corresponding target, the overlay error can be deduced 530.

Table 1 illustrates how this may be done. The smallest measured overlay in the example shown is −1 nm. However this is in relation to a target with a programmed overlay of −30 nm. Consequently the process must have introduced an overlay error of 29 nm.

TABLE 1

| | | | | | | | |
|---|---|---|---|---|---|---|---|
| Programmed Overlay | −70 | −50 | −30 | −10 | 10 | 30 | 50 |
| Measured Overlay | −38 | −19 | −1 | 21 | 43 | 66 | 90 |
| Difference between Measured and Programmed Overlay. | 32 | 31 | 29 | 31 | 33 | 36 | 40 |
| Linearity Error | 3 | 2 | — | 2 | 4 | 7 | 11 |

As the previously, this smallest value can be taken to be the reference point and, relative to this, the offset can be calculated between measured overlay and that expected due to the programmed overlay. This offset determines the linearity error. Therefore, in the Table 1 example, the smallest measured overlay was −1 nm, at the target position with programmed overlay of 30 nm. The difference between the expected and measured overlay at the other targets is compared to this reference. Once adjustments for the overlay error introduced by the machine are made, the differences between the measured overlay and the expected overlay relate to the linearity error.

Back to FIG. 6, as a table such as Table 1 is obtained for different illumination settings, the illumination setting which results in the smallest linearity error, and its corresponding calibration factor, can be determined and selected 540. Following this, the Total Measurement Uncertainty (TMU) can be obtained for this calibration factor and smallest linearity error, for different wavelengths and/or polarizations and/or aperture dimensions, to find the best TMU with the smallest linearity error. The real wafer measurement 550 is then performed with the best settings to achieve this TMU, and the determined calibration factor.

Figure 7:
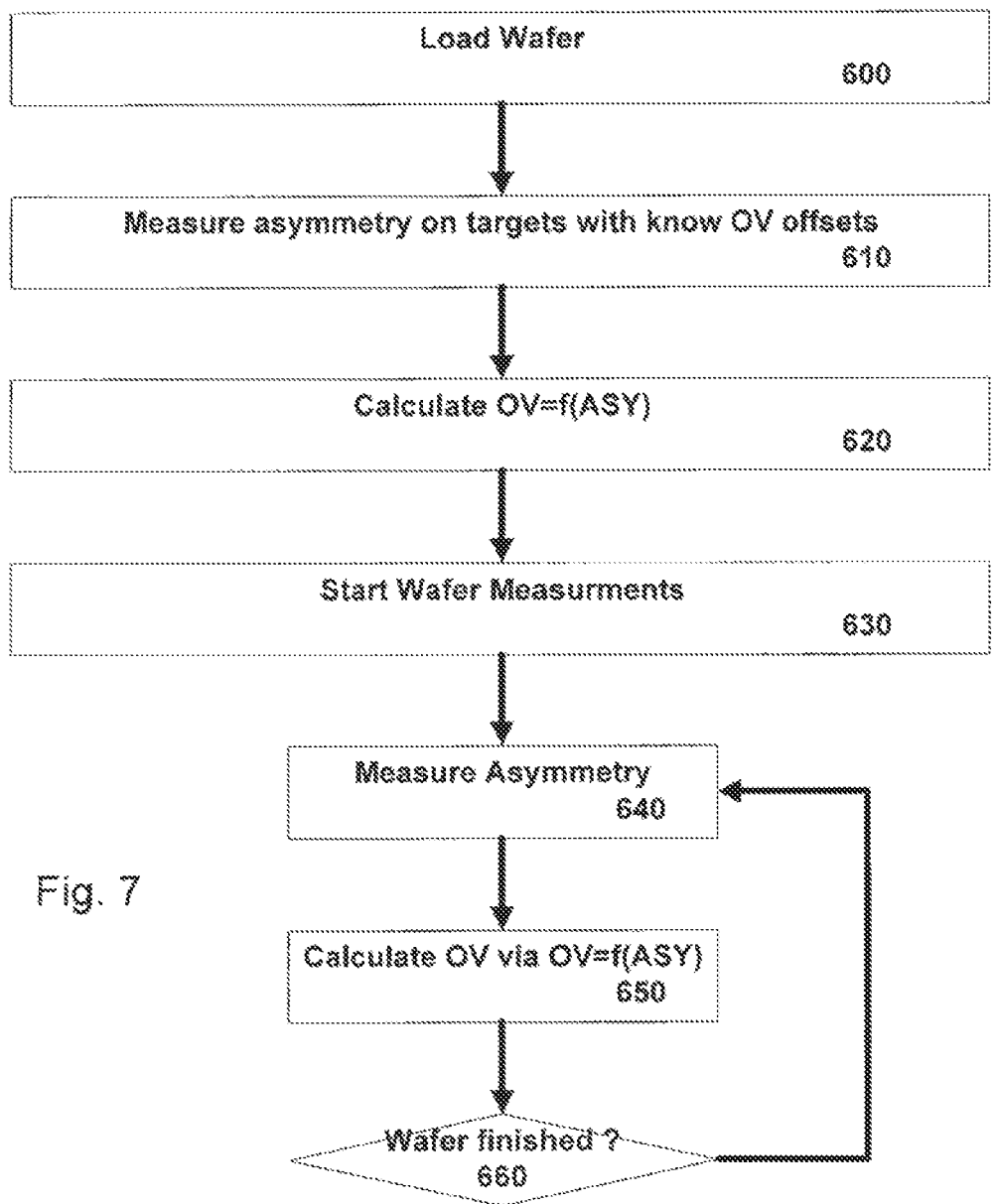
FIG. 7 is a flowchart illustrating a method according to a second embodiment of the invention.

FIG. 7 is a flowchart illustrating another embodiment of the invention. In this example, the calibration targets are gratings with an induced offset between layer one and two perpendicular to the grating lines. This simply represents a different way to bias the targets, they can either be biased symmetrically around the origin or an overlay offset (offset+/− bias) can be introduced.

The wafer is loaded 600 and all the asymmetries with the known offsets are measured and plotted against their corresponding programmed overlay offsets 610. The programmed overlay number at the point were asymmetry equals zero, that is the point were there is zero measured overlay, represents the overlay error induced by the scanner during printing, and is therefore subtracted from the programmed overlay numbers. The final curve can be fitted with a higher order polynomial function or Fourier series so as to obtain a formula 620 that represents the overlay versus asymmetry curve without linearity error. During the wafer measurement 630, the asymmetry is measured for each point 640 and function determined at step 620 is used to determine overlay from asymmetry (without linearity error) 650. This is done for every point to be measured until the wafer is finished 660.

As the shape of the plot of higher order asymmetry against overlay is known, targets during the wafer measurement do not require biased gratings anymore, and targets with one grating in one direction are sufficient. This allows throughput to be effectively doubled in comparison to the first described embodiment, as less measurements in total are required. By way of example, a typical baseliner sample scheme is 25 pts per field, 75 Fields; using 2 Targets (with positive and negative bias). This results in 3750 measurements. However, using this method in a best case scenario: 1 calibration set, e.g., 11 targets, 2 acquirements=22 acquirements. It is now sufficient to measure only one grating on the rest of the wafer, which amounts to 1875 measurements. Therefore total number of measurements is 1875+22=1887.

Conventionally, finding the best setting by involves finding a compromise between good Total Measurement Uncertainty (TMU) and low linearity error (accuracy and precision). As the above embodiment means that there is no longer a linearity error, the calibration being done for every wavelength, the best measurement wavelength can simply be evaluated via TMU. Also, given the model and the measurement uncertainty, one can determine the uncertainty in the overlay calculation. This uncertainty can be used as a metric to determine how many markers need to be placed and at what induced offset.

The above methods can result in the following.

The exact relation between asymmetry and overlay can be determined and used to correct the measurements without extra measurements (on IBO tools) or extra scanner exposures (with programmed overlay)

Reduced overhead, as no data from other calibration wafers needs to be stored and assigned to specific lots Parameter setup requires only typing in the right target position, as the best illumination setting selection can be done on regular bases automatically (e.g., in the lot overhead)

Improved process robustness as the parameter setup selection and calibration are done on regular bases (e.g., when the stack parameters change)

In the latter embodiment, improved throughput performance and smaller targets in the field (no bias needed).

Figure 8:
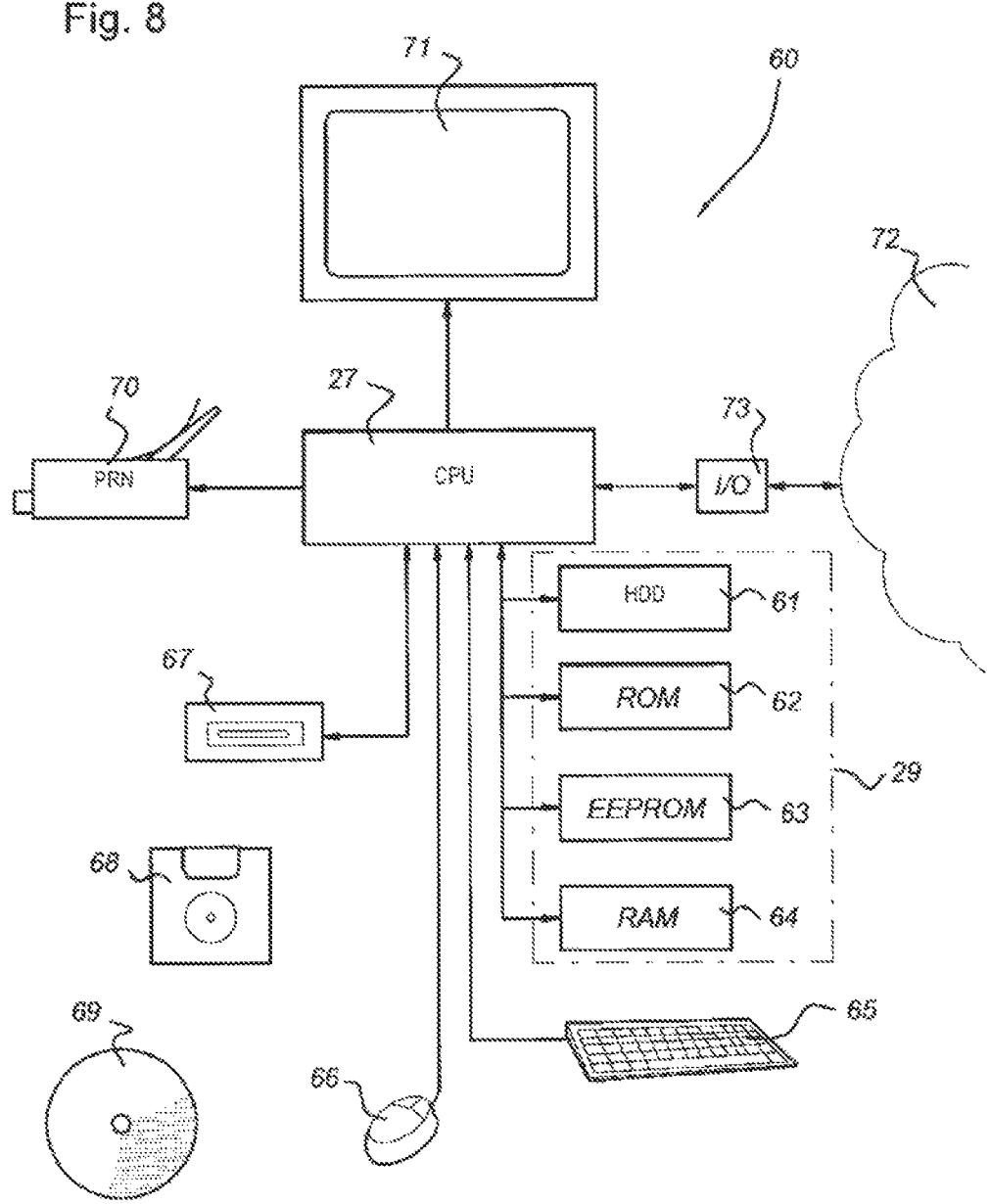
FIG. 8 depicts a computer assembly that may be used in apparatus according to an embodiment of the present invention.

It should be understood that the asymmetry processor 91 and the overlay calculation processor 92 may be implemented in one or more computer assembly 60 as shown in FIG. 8. The computer assembly 60 may be a dedicated computer in the form of an asymmetry processor 91 or an overlay calculation processor 92 in embodiments according to the invention or, alternatively, be a central computer controlling the lithographic apparatus. The computer assembly 60 may be arranged for loading a computer program product comprising computer executable code. This may enable the computer assembly 60, when the computer program product is downloaded, to control aforementioned uses of lithographic and inspection apparatuses.

The memory 29 connected to processor 27 may comprise a number of memory components like a hard disk 61, Read Only Memory (ROM) 62, Electrically Erasable Programmable Read Only Memory (EEPROM) 63 or Random Access Memory (RAM) 64. Not all aforementioned memory components need to be present. Furthermore, it is not essential that aforementioned memory components are physically in close proximity to the processor 27 or to each other. They may be located at a distance away.

The processor 27 may also be connected to some kind of user interface, for instance a keyboard 65 or a mouse 66. A touch screen, track ball, speech converter or other interfaces that are known to persons skilled in the art may also be used.

The processor 27 may be connected to a reading unit 67, which is arranged to read data, e.g., in the form of computer executable code, from and under some circumstances store data on a data carrier, like a floppy disc 68 or a CDROM 69. Also DVD's or other data carriers known to persons skilled in the art may be used.

The processor 27 may also be connected to a printer 70 to print out output data on paper as well as to a display 71, for instance a monitor or LCD (Liquid Crystal Display), of any other type of display known to a person skilled in the art.

The processor 27 may be connected to a communications network 72, for instance a public switched telephone network (PSTN), a local area network (LAN), a wide area network (WAN) etc. by means of transmitters/receivers 73 responsible for input/output (I/O). The processor 27 may be arranged to communicate with other communication systems via the communications network 72. In an embodiment of the invention external computers (not shown), for instance personal computers of operators, can log into the processor 27 via the communications network 72.

The processor 27 may be implemented as an independent system or as a number of processing units that operate in parallel, wherein each processing unit is arranged to execute sub-tasks of a larger program. The processing units may also be divided in one or more main processing units with several subprocessing units. Some processing units of the processor 27 may even be located a distance away of the other processing units and communicate via communications network 72.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method comprising:
   measuring asymmetry of radiation reflected from each of a plurality of targets on a substrate, each of the plurality of targets comprising a predetermined overlay offset;

identifying a target of the plurality of targets at which the measured asymmetry equals zero;

determining the overlay error of a point on the substrate as a function of measured asymmetry reflected from the point, wherein the function is determined by fitting a polynomial or a Fourier series to a comparison of the measured asymmetry of the radiation reflected from each of the plurality of targets to a difference of the corresponding predetermined overlay offset of the respective target and the predetermined overlay offset of the identified target, and wherein the function limits an effect of linearity error; and adjusting a parameter of the lithographic apparatus before subsequent processing on a same layer or another layer based on a determined overlay error of the point.

2. The method of claim 1, wherein the comparing the measured asymmetry of the radiation reflected from each of the plurality of targets to the corresponding predetermined overlay offset of the respective target comprises plotting the measured asymmetry of the radiation reflected from each of the plurality of targets against the corresponding predetermined overlay offset of the respective target; and wherein the function is determined by fitting the higher order polynomial or the Fourier series to the plot of the measured asymmetry of the radiation reflected from each of the plurality of targets against the corresponding predetermined overlay offset of the respective target.

3. The method of claim 1, wherein the plurality of targets each comprises a grating with the predetermined offset being between first and second overlapping patterns.

4. The method of claim 1, wherein the plurality of targets comprises a positive bias, a negative bias, or both a positive bias and a negative bias.

5. The method of claim 1, further comprising:

obtaining a Total Measurement Uncertainty (TMU) for the function at different illumination settings; and selecting an illumination setting that results in the smallest TMU.

6. The method of claim 1, wherein the function is determined by fitting the Fourier series to the comparison of the measured asymmetry of the radiation reflected from each of the plurality of targets to the corresponding predetermined overlay offset of the respective target.

7. An inspection apparatus comprising:

a projector configured to project radiation onto a point on a substrate and onto a plurality of targets having a respective predetermined overlay offset;

a detector configured to detect radiation reflected from the point on the substrate and from the plurality of targets; and a processor configured to:

measure asymmetry of the radiation reflected from the point on the substrate and from the plurality of targets; and determine the overlay error of the point on the substrate as a function of the measured asymmetry of the radiation reflected from the point on the substrate, wherein the function limits an effect of linearity error, and wherein the function is determined by fitting a polynomial or a Fourier series to a comparison of measured asymmetry of radiation reflected from each of the plurality of targets to a difference of the corresponding predetermined overlay offset of the respective target and the predetermined overlay offset of a target of the plurality of targets at which the measured asymmetry equals zero.

8. The inspection apparatus of claim 7, wherein the comparison is a plot of the measured asymmetry of the radiation reflected from each of the plurality of targets against the corresponding predetermined overlay offset of the respective target.

9. The inspection apparatus of claim 7, wherein the plurality of targets each comprise a grating with the predetermined offset being between first and second overlapping patterns.

10. The inspection apparatus of claim 7, wherein the plurality of targets comprise a positive bias, a negative bias, or both a positive bias and a negative bias.

11. The inspection apparatus of claim 7, wherein the processor is further configured to obtain a Total Measurement Uncertainty (TMU) for the function at different illumination settings; and select an illumination setting that results in the smallest TMU.

12. The inspection apparatus of claim 7, wherein the function is determined by fitting the Fourier series to the comparison of the measured asymmetry of the radiation reflected from each of the plurality of targets to the difference of the corresponding predetermined overlay offset of the respective target and the predetermined overlay offset of the identified target.

13. A non-transitory computer readable medium comprising one or more sequences of machine-readable instructions enabling an apparatus to perform operations comprising:

measuring asymmetry of radiation reflected from each of a plurality of targets on a substrate, each of the plurality of targets comprising a predetermined overlay offset;

identifying a target of the plurality of targets at which the measured asymmetry equals zero;

determining an overlay error of a point on the substrate other than at the plurality of targets as a function of measured asymmetry reflected from the point, wherein the function is determined by fitting a higher order polynomial or a Fourier series to a comparison of the measured asymmetry of the radiation reflected from each of the plurality of targets to a difference of the corresponding predetermined overlay offset of the respective target and the predetermined overlay offset of the identified target, and wherein the function limits an effect of linearity error, and adjusting a parameter of the lithographic apparatus before subsequent processing on a same layer or another layer based on a determined overlay error of the point.

14. The non-transitory computer readable medium of claim 13, further comprising plotting the measured asymmetry of the radiation reflected from each of the plurality of targets against the difference of the corresponding predetermined overlay offset of the respective target and the predetermined overlay offset of the identified target; and wherein the function is determined by fitting the higher order polynomial or the Fourier series to the plot of the measured asymmetry of the radiation reflected from each of the plurality of targets against the difference of the corresponding predetermined overlay offset of the respective target and the predetermined overlay offset of the identified target.

15. The non-transitory computer readable medium of claim 13, wherein the operations further comprise:

obtaining a Total Measurement Uncertainty (TMU) for the function at different illumination settings; and selecting an illumination setting that results in the smallest TMU.

16. The non-transitory computer readable medium of claim of claim 13, wherein the function is determined by fitting the Fourier series to the comparison of the measured asymmetry of the radiation reflected from each of the plurality of targets to the difference of the corresponding predetermined overlay offset of the respective target and the predetermined overlay offset of the identified target.

\* \* \* \* \*